(12) United States Patent
Buchner

(10) Patent No.: US 7,844,339 B2
(45) Date of Patent: *Nov. 30, 2010

(54) PROCEDURE AND MACHINE FOR ELECTRO-INDUCING/STIMULATING DEEP LAYERED MUSCLE CONTRACTIONS USING A BIPHASIC FARADIC PULSE SEQUENCE

(76) Inventor: Kelly W. Buchner, 3171-A S. 129th E. Ave., Tulsa, OK (US) 74134

( * ) Notice: Subject to any disclaimer, the term of this patent is extended or adjusted under 35 U.S.C. 154(b) by 1613 days.

This patent is subject to a terminal disclaimer.

(21) Appl. No.: 10/840,064

(22) Filed: May 6, 2004

(65) Prior Publication Data

US 2005/0033387 A1 Feb. 10, 2005

Related U.S. Application Data

(63) Continuation of application No. 10/131,376, filed on Apr. 24, 2002, now Pat. No. 6,745,078.

(51) Int. Cl.
*A61N 1/00* (2006.01)
(52) U.S. Cl. .......................................... 607/46; 607/72
(58) Field of Classification Search ............. 607/46–52, 607/69–76
See application file for complete search history.

(56) References Cited

U.S. PATENT DOCUMENTS

| 5,397,338 A | * | 3/1995 | Grey et al. ................. 607/115 |
| 6,029,090 A | | 2/2000 | Herbst |
| 6,094,599 A | | 7/2000 | Bingham |

OTHER PUBLICATIONS

The Diabetic Foot, Levin,M.F., M.D., C.W. Mosky,Co., 1993.
Blood Viscosity, Dintenfass,Leoppold, PhD., MTP Press Limited, 1985.
Clinical Hemorheology, S. Chien, Martinus Nijhoff, 1987.
Dintefass, Leopold, PhD.: The Clinical Impact of the Newer Research in Blood Rheology: An Overview. Angiology. vol. 32, No. 4, Apr. 1981, pp. 217-229.
Dintefass, Leopold, PhD.: Hemorheology of Diabetes Mellitus. Advances in Micro Circulation. vol. 8, pp. 14-36, 1979.
Simpson, Leslie O., PhD.: Altered Blood Rheology in the Pathogenesis of Diabetic and Other Neuropathies, Muscle and Nerve, 11:725-744, 1988.
Vascular Medicine, Loscano, Greater, Dlau Little Brown & Co., 1990.
Physiology of the Human Body, Guyton, Arthur C., Holt Rinehartr & Winston, 1984.

* cited by examiner

*Primary Examiner*—Scott M Getzow
(74) *Attorney, Agent, or Firm*—Gable & Gotwals

(57) ABSTRACT

A procedure and machine promotes healing by causing muscle fasciculation and contraction relaxation cycles that effectively pump blood through the microcirculation, draining the venous beds and raising the tissue oxygen levels. A high phase charged system is electronically pulsed and adjusted to induce deep-layered muscle contractions, causing greatly increased flow rates of both blood and lymphatics, patency of vessels permitting, and forcing blood into the microcirculation of the treated tissue. The machine electrical waveform stimulates angiogenesis, facilitating new tissue growth and repair in the healing process and raises the metabolic rate in the treated tissues.

11 Claims, 10 Drawing Sheets

PROCEDURE AND MACHINE FOR ELECTRO-INDUCING/STIMULATING DEEP LAYERED MUSCLE CONTRACTIONS USING A BIPHASIC FARADIC PULSE SEQUENCE

This application is a continuation of application Ser. No. 10/131,376, filed Apr. 24, 2004 for "Procedure and Machine for Electro-Inducing/Stimulating Deep Layered Muscle Contractions Using a Biphasic Faradic Pulse Sequence."

BACKGROUND OF THE INVENTION

This invention generally relates to therapeutic treatment of human and animal tissues and more particularly concerns a procedure and machine for electro-inducing or stimulating deep layered muscle contractions in tissues for the purpose of healing and treating wounds and various vascular deficiency ailments such as peripheral vascular disease, ischemic rest pain, diabetic neuropathy, pressure ulcers, slow or non-healing wounds, chronic low back pain, osteoarthritis, occupational problems such as carpal-tunnel syndrome, tendonitis and other sports injuries.

An underlying characteristic of the above conditions and diseases is impaired circulation in the capillary beds as well as nerve damage. Without blood flow to the tissues, oxygen and nutrients cannot get into the tissues and the waste products of metabolism cannot get out. This puts a severe stress on the tissues causing them to go into a survival mode. The cells use what limited resources they have to stay alive and higher functions, including healing and repair, as well as tissue mediated immunity, become essentially shut down. In most patients with severe disease, measured tissue oxygen levels have been found to be less than 15% of normal. Diabetics with impaired basement membrane function, Reynauds phenomena, Claudication states and other similar conditions all may have similar features due to this underlying characteristic.

Essentially, every tissue in the body has intrinsic electrical properties. Because of this, it has been found that they respond to electrical stimulation. There have been many machines designed over the years to use electricity to affect the body in various ways to enhance the healing process. There are many variables in the use of electricity, including polarity, voltage, amperage, frequency and waveform. Although there are a variety of alternate technologies available today, the electronic parameters of known machines have limited applications.

Hyperbaric oxygen therapy has been shown to be effective in healing ischemic ulcers. 100% oxygen at 2 atmospheres will give a partial pressure of oxygen 10 times normal. This greatly increases the rate of diffusion through the open face of the ulcer. Skin, however, is not as permeable to oxygen diffusion and oxygen delivery depends upon intact circulation as well. Hyperbaric oxygen therapy is a passive process and does not alter the underlying disease in the microcirculation.

There are several procedures in practice using moist heat with occlusion dressings, infrared lamps, membranes with electrical currents and warm water whirlpool treatments. These have all shown some merit and have been effective in varying degrees. They all work by stimulating the arterioles in the capillary beds to dilate in response to infrared energy. These also are passive procedures, however, and do not alter the underlying disease in the microcirculation.

Machines using high frequency interferential electrical currents are also effective. They stimulate the nerves in the skin and cause dilation of the capillary beds through the reflex pathways. However, this form of electrical current tends to be more superficial in the tissues and, therefore, less decisive and rapid in its healing effects.

Another procedure being used today consists of a garment placed around the diseased limb. Intermittent compression is then administered via compressed air from the attached machine. This again has proven to be effective to promote circulation and healing by pumping the blood through the capillary beds. Pressure gradients are increased in the capillary beds but there is not necessarily the dilation of the arterioles as the other methods promote. This procedure does not remodel the microcirculation either.

It is, therefore, an object of this invention to provide an electrical tissue treating procedure and machine which increases circulation in capillary beds. Another object of this invention is to provide an electrical tissue treating procedure and machine which significantly remodels microcirculation so as to provide more permanent therapeutic improvement. A further object of this invention is to provide an electrical tissue treating procedure and machine which not only dilates arterioles but also increases pressure gradients across the capillary beds to improve flow and oxygen levels and promote angiogenesis. Yet another object of this invention is to provide an electrical tissue treating procedure and machine which provides deep layered muscle contractions and perfuses tissues with blood so as to afford more decisive and rapid healing than known methods and machines. It is also an object of this invention to provide an electrical tissue treating procedure and machine which facilitates more rapid and decisive healing of vascular deficiency ailments than known procedures and machines.

SUMMARY OF THE INVENTION

In accordance with the invention, a procedure and machine are provided to promote healing by causing muscle fasciculation and contraction relaxation cycles that effectively pump blood through the microcirculation, draining the venous beds and raising the tissue oxygen levels. This, in turn, supplies the oxygen and substrates necessary to greatly accelerate the healing process. Pressure gradients are actually increased across the capillary beds with perfusion of blood into the designated area of the patient, in contrast to merely dilating the capillary beds. Therefore, the treatment has a potent effect on the microcirculation, which results in dramatic responses to treatment. Transcutaneous oxygen monitors have demonstrated marked increases in tissue oxygen levels within minutes of initiating treatment. Tissue oxygen levels with successive treatments continue to improve.

A high phase charged system is electronically pulsed and adjusted to induce deep-layered muscle contractions, causing greatly increased flow rates of both blood and lymphatics, patency of vessels permitting, and forcing blood into the microcirculation of the treated tissue.

The machine electrical waveform stimulates angiogenesis, that is, budding of new capillaries and generation of denser capillary networks in the tissues. This lays the groundwork for new tissue growth and repair in the healing process. The machine electrical waveform also raises the metabolic rate in the treated tissues, which, it is theorized, helps the intimal lining of the arteries to metabolize the excess unused nutrients clogging them. Whatever the actual cause, the effect is improved blood flow that has been shown to be permanent, particularly in patients with neuropathy.

The procedure and machine have been tested on diabetics with severe ischemic ulcers in feet that were destined for amputation. This condition is usually associated with underlying osteomeyelitis, which does not respond well to standard therapy including systemic antibiotics and wound care. The present treatment greatly improves the management of this condition because the enhanced blood flow brings enhanced levels of antibiotics and healing to the affected area. In almost every case, the feet have been salvaged.

In addition, the machine's electrical waveform directly stimulates the activity of fibroblasts in the healing process. In the healing of ischemic ulcers the fibroblasts act first to build the framework upon which further cell types including skin and capillaries grow. The electrical current is a deep penetrating current that affects all tissues from the skin to the bone. Technically, the machine generates an electromagnetic field between the emitter pads, in contrast to the electrical waveform of some machines that stay rather superficial in the tissues affecting primarily the top several millimeters. The system stimulates activity in bone cells as well, which accelerates fracture healing.

Finally, the procedure and machine have achieved excellent test case success in reversing neuropathy in the feet and legs of diabetics being treated. In follow up on this condition thus far, improvement has persisted for extended periods of time. There is no other known technology or treatment modality that has reversed diabetic neuropathy. The reason for this unique therapeutic benefit is not known. It may be due to improvement in the circulation that nourishes the nerves or due to an unknown direct action on the nerves themselves.

The procedure and machine have shown remarkable efficacy in dealing with the above difficult disease states. In comparison with the current alternative technologies on the market today, the present treatment has proven to cause more rapid and decisive healing. In addition, the patients have enjoyed permanent, persistent improvements in the circulation of the affected limb.

A treatment regimen of forty-five minutes a day has been effective in a very high percentage of patients treated resulting in remarkable changes in both neural conductivity and wound healing rates. Most importantly, patients report a high level of comfort with treatment.

Even with a relatively high phase charge, the comfort level to the patient remains acceptable over extended periods of time, during which the muscle groups are contracting. During moderate muscle contraction, blood rates can increase from 10 to 25 times the patient's resting blood flow. While only 20 to 25 percent of muscle capillaries are open during rest, nearly all of the dormant capillaries open up during moderate muscle contraction. Because of the decreased oxygen concentration in the tissue fluid (because of increased oxygen demands from the contracting muscles), vasodilation of the vessels is triggered by release of adenosine and other vasodilator substances, to the extent that any vasodilation is possible. In addition, lymph will not flow freely from resting muscle. However, the contracting muscles will squeeze or pump the lymph vessels and capillaries resulting in increased flow rates. With this increased fluid perfusion due to passive repetitive contractions (static work, an unopposed, involuntary muscle contraction) there is little lactic acid build up and most importantly there is more oxygenated blood, due to the pumping action of the muscles exerted on the arterial side.

As an example, take the lower leg as an area to be treated for healing a diabetic ulcer on the foot. The emitter pads are applied to the anterior and posterior muscle compartments of the lower leg. This will achieve muscle contractions in the anterior compartment, consisting of the anterior tibial and the extensor group and of the posterior compartment consisting of the gastrosoleus, flexors and peroneals. As these muscles pump oxygenated blood to the tibial and peroneal arteries and their smaller branches, the velocity and flow increases. The viscosity of the blood decreases and the red blood cells reach a desirable state of deformability. These erythrocytes are able, with increased velocity and ellipsoidal shape, to reach tissue they were blocking or unable to migrate through previously. In addition to the enhanced perfusion of compromised tissues, the increase in blood flow and passive exercise in often debilitated muscles, reduces the effects of muscle disuse atrophy. This sets in motion a therapeutic cycle of increased mobility by the patient. When walking and weight bearing is desirable, the patient is literally contributing to their own improvement in circulatory status by increased walking and well-being.

Prior to the procedure and machine herein described, there are well-defined protocols for treatment of wounds. Many of these same protocols are followed in conjunction with the present methods. A similar example obtains with chemotherapy in the treatment of malignant tumors. In chemotherapy, besides attacking the target tumor, there are numerous undesirable side effects. The side effects would be less if the chemotherapy dosage were reduced. The effect on the tumor would also be reduced, unless there were some means to make the tumor more susceptible to the chemotherapy. It is found that the present methods have precisely that effect by increasing fluid perfusion in the tumor and the vicinity thereof.

BRIEF DESCRIPTION OF THE DRAWINGS

Other objects and advantages of the invention will become apparent upon reading the following detailed description and upon reference to the drawings in which.

While the invention will be described in connection with a preferred embodiment, it will be understood that it is not intended to limit the invention to that embodiment. On the contrary, it is intended to cover all alternatives, modifications and equivalents as may be included within the spirit and scope of the invention as defined by the appended claims.

DETAILED DESCRIPTION

The machine applies the output of a biphasic faradic pulse generator to one or more sets of conductor pads oppositely applied to the area to be treated.

Figure 1:
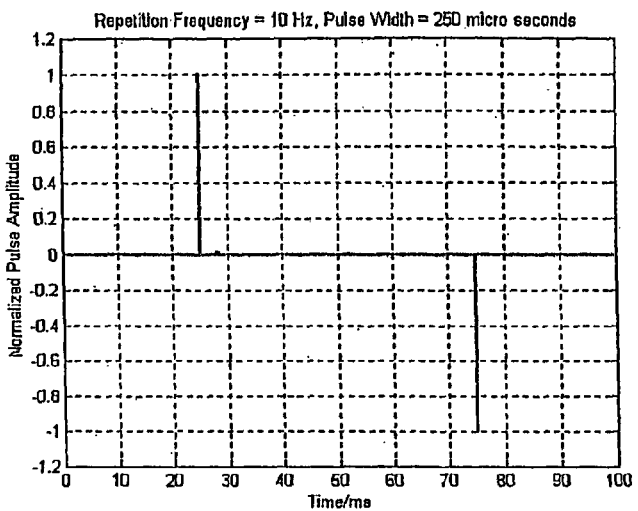
FIG. 1 is a graphic representation of a typical computer generated biphasic pulse sequence.
Figure 2:
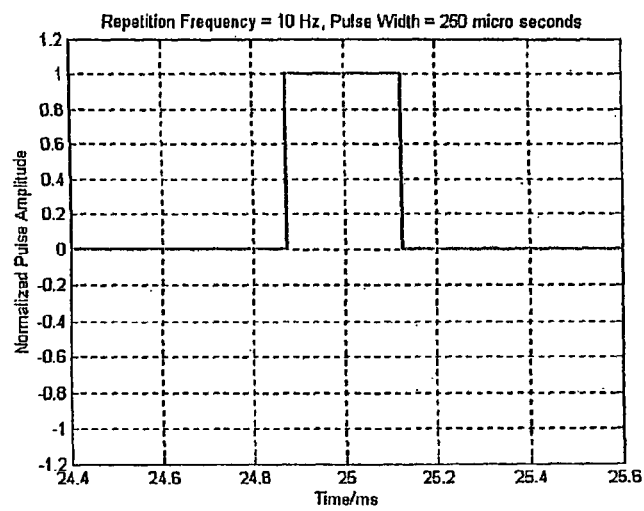
FIG. 2 is an expanded time scale representation of the positive pulse of FIG. 1.

The following waveform analysis, based on use of computer generated biphasic pulses, was used to select and evaluate the waveform of the generated pulse. It is believed that the benefits of electro-stimulation are related to the stimulation frequency components (see, e.g. Savage, Brenda, "Inferential Therapy," Faber and Faber, London, 1984). Considering the biphasic pulse of FIG. 1 and expanding the time scale about the positive pulse as shown in FIG. 2, it is seen to be a well-formed rectangular pulse. This pulse validates the frequency analysis which is to follow with respect to the frequency spectral content of the biphasic waveform. For the most part, the periods of the biphasic pulses are short in terms of the period of the overall pulse sequence, so the spectrum of the overall sequence can be represented by a Fourier series. Analytically, this is given by $$p(t) = \sum_{n=1}^{\infty} P(f_n) \sin 2\pi f_n t$$

Where $P(f_n)$ is the magnitude of the n-th frequency component, given by $$P(f_n) = \frac{4}{T} \left[ \frac{\sin(2\pi \frac{\tau}{2} f_n)}{2\pi \frac{\tau}{2} f_n} \right] \sin\left(2\pi \frac{T}{4} f_n\right) \text{ where}$$

$\tau$=the individual pulse width and T=the biphasic pulse period

The first thing to note is that in frequency space, the factor in the brackets is a relatively low frequency envelope acting on the higher frequency term outside the brackets. This is exemplified by FIG. 3. The spectrum is shown only out to 100 kHz.

The period of the envelope is set by the individual pulse widths and the period of the high frequency components interior to the envelope are set by the biphasic pulse period. This is the amplitude spectrum used to produce FIGS. 1 and 2. To get the clean pulses previously shown it was necessary to use frequencies out to 1 MHZ. Typical of Fourier series, the convergence is rather slow.

Figure 3:
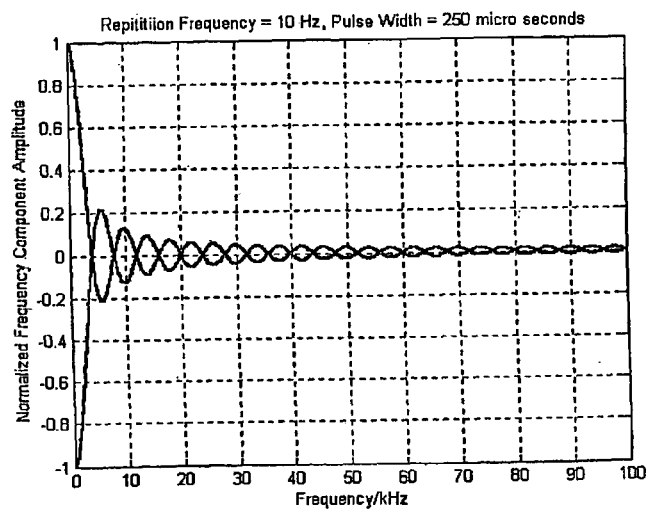
FIG. 3 is a graphic representation of the amplitude spectrum of the biphasic pulse sequence of FIG. 1.
Figure 4:
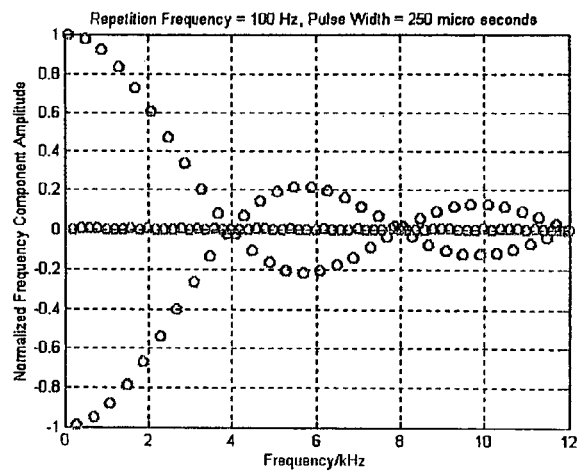
FIG. 4 is an expanded frequency scale representation of the low frequency portion of the amplitude spectrum with an increased repetition rate.

To get a better picture of a typical spectrum, the magnitude of the lowest frequency can be increased by increasing the pulse repetition rate, as indicated in FIG. 4. In FIG. 4, the actual values of the frequency component amplitudes are indicated by the circles. The continuous lines are only a visual aide. The high frequency components interior to the envelope have been spread. In the previous spectrum, the high frequency components were so closely packed that they appeared to be solid. The spectrum is actually discrete. In FIGS. 3 and 4, all positive spectral components are followed by a zero amplitude component and a negative going component, and conversely for all negative going components. There are multiples of the fundamental missing.

Figure 5:
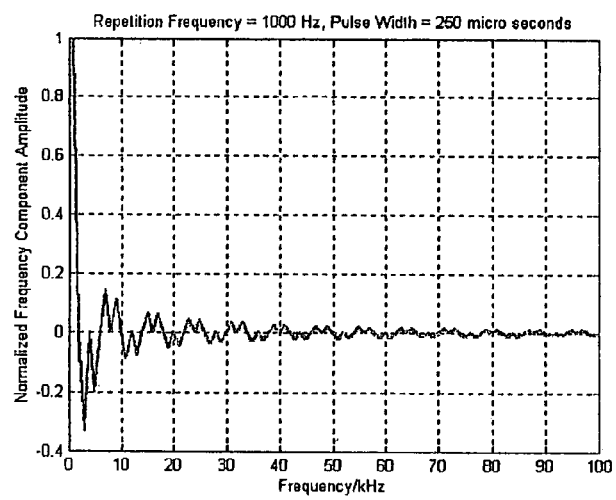
FIG. 5 is an expanded amplitude graphic representation of the positive amplitude portion of the amplitude spectrum at the highest repetition rate.
Figure 6:
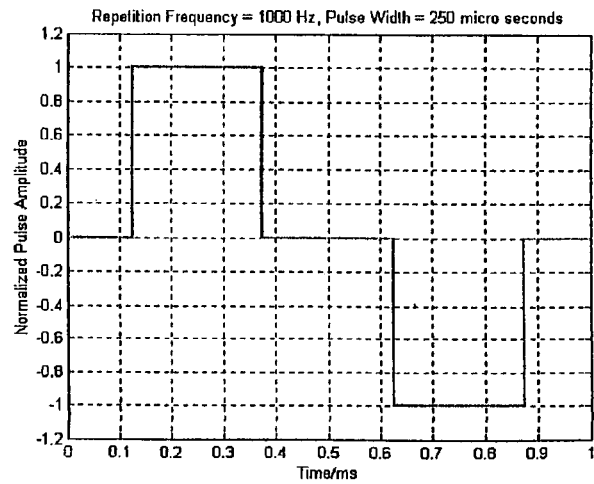
FIG. 6 is a graphic representation of the biphasic pulse corresponding to the amplitude spectrum of FIG. 5.

Turning to FIG. 5, the biphasic pulse period is reduced to its lower limit with the pulse width at its upper limit. There is one dominant frequency component with minimal high frequency content, as might be expected, considering that the corresponding biphasic pulse is beginning to approximate a pure sinusoid, as is shown in FIG. 6.

Figure 7:
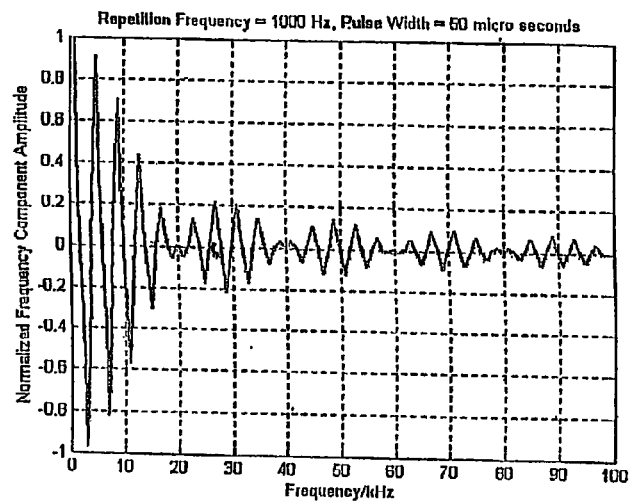
FIG. 7 is a graphic representation of the amplitude spectrum of a biphasic pulse sequence having a different pulse width than the pulse width of the sequence of FIG. 6.

The above analysis shows, by reference to FIG. 5, that the lowest frequency available is 1 kHz with minimal higher frequency content. This also applies to FIG. 7 where the lowest frequency available is set by the biphasic repetition rate. For this repetition rate, changing the pulse width has minimal effect.

Figure 8:
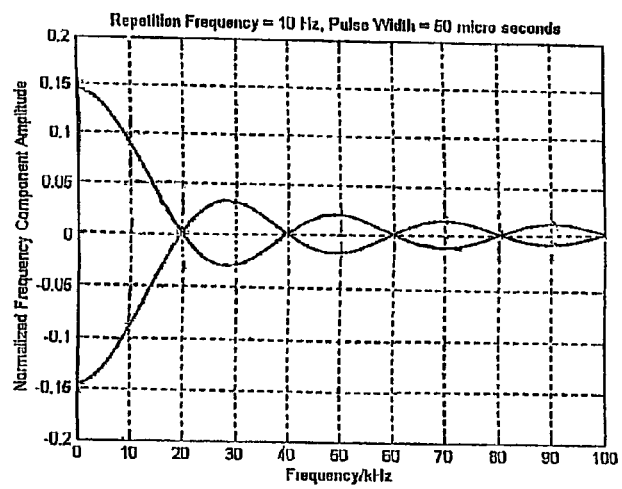
FIG. 8 is a graphic representation of the amplitude spectrum of a biphasic pulse sequence having a narrower pulse width than the pulse width of the sequence of FIG. 6.

Considering the situation with the lowest pulse repetition rate as shown in FIG. 3, there is much higher concentration of the pulse energy at the lower frequencies with a substantial amount of energy at the higher frequencies. Looking at FIG. 8, the narrowing of the pulse has spread the frequencies to higher values. The lowest frequency is 10 Hz.

Interferential therapy tells us that, " . . . for each type of excitable tissue there is an optimum frequency at which the maximum response will be obtained." (Savage, op.cit.) The frequencies lie between 0 and 130 Hz. The lower frequency repetition rates appear to be the most favorable. An infinite pulse train has been assumed, an assumption which is worst for the lower repetition rates. Resolution of this assumption will render the spectrum continuous rather than discrete. The most favorable pulse sequence appears to be 10 Hz repetition and 250 µs pulse width, although some of the region below 10 Hz would be lost. However, the spread spectrum permits a large number of tissue types to be affected.

Figure 9:
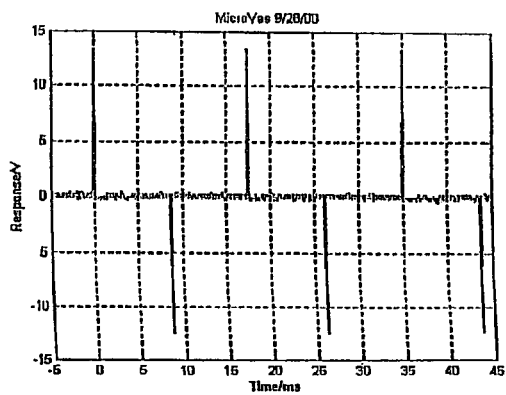
FIG. 9 is a graphic representation of a portion of a measured biphasic pulse sequence used in system analysis of the machine.

Following the above computer generated waveform analysis, measured data was obtained using prototypes of the machine. The data was measured at is full intensity into a load of 50Ω. The output of the system was a sequence of biphasic pulses, with a sequence duty cycle of 1.5 seconds on and 1.5 seconds off. A portion of one sequence is shown in FIG. 9, having a biphasic period of 17.5 ms and a repetition frequency of 57 Hz. In 1.5 seconds, the machine delivers 86 biphasic pulses to the patient.

Figure 10:
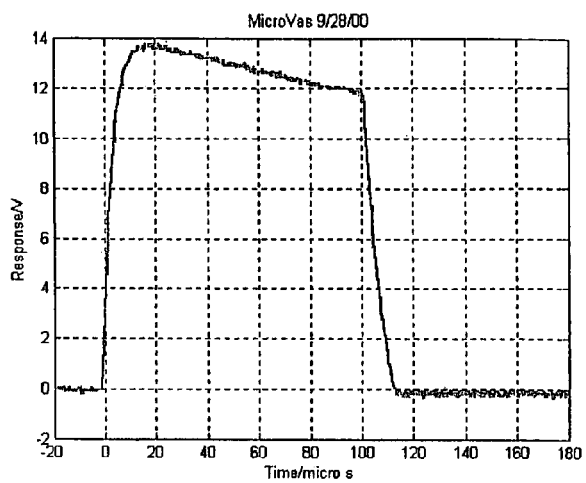
FIG. 10 is an expanded time scale graphic representation of the positive half of the pulse sequence of FIG. 9.
Figure 11:
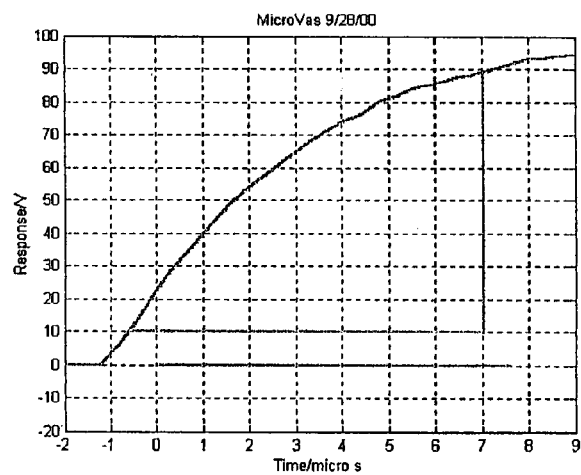
FIG. 11 is an expanded time scale graphic representation of the leading edge of the positive pulse of FIG. 10.
Figure 12:
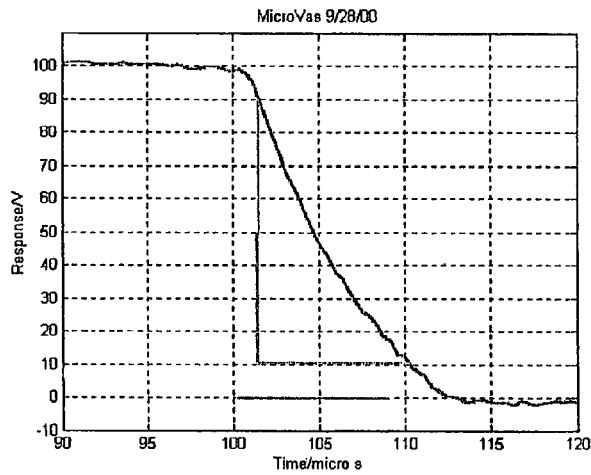
FIG. 12 is an expanded time scale graphic representation of the trailing edge of the positive pulse of FIG. 10.

The positive half of the biphasic pulse is shown in FIG. 10 and has a zero-to-zero pulse width of 110 µs. The leading edge, displayed on an expanded time scale in FIG. 11, has a 10 to 90 percent rise time of just under 8 µs. The trailing edge, seen in FIG. 12, has a fall time of 9 μs. The negative going half has essentially the same characteristic as the positive going half.

Two key parameters concerning the interaction of the system with the patient are the open circuit voltage and internal impedance. There are two ways of changing the system loading: placing a resistance in series or placing a resistor in parallel.

The following parameters are assumed:
$V_O$=Microvas open circuit voltage
$R_S$=Microvas source resistance
I=Microvas current
$R_O$=measurement system input impedance
$R_L$=The added load resistance
$V_m$=The voltage at the measurement system input In the series load case, the Microvas current is given by I=$V_m$/$R_O$ with the Kirchoff equations $$V_O - I_1 R_S = I_1 (R_{L1} + R_O)$$

$$V_O - I_2 R_S = I_2 (R_{L2} + R_O)$$

The immediate determanantal solution is $$R_s = \frac{I_2(R_{L2} + R_o) - I_1(R_{L1} + R_o)}{I_1 - I_2} \text{ and } V_o = \frac{I_1 I_2}{I_1 - I_2}(R_{L2} - R_{L1})$$

In the parallel case, the Microvas current is given by $$I = \frac{V_m(R_L + R_o)}{R_L R_o}$$

with Kirchoff equations $$V_O - I_1 R_S = V_{m1}$$

$$V_O - I_2 R_S = V_{m2}$$

Again, an immediate determanantal solution is given by $$R_s = \frac{V_{m2} - V_{m1}}{I_1 - I_2} \text{ and } V_o = \frac{I_1 V_{m2} - I_2 V_{m1}}{I_1 - I_2}$$

The measurements were made with an oscilloscope preceded by a 40 dB attenuator. The input impedance of the system is 50Ω. Thus the parallel case can only vary the effective loading of the Microvas from 0 to 50Ω. In use, it appears that the expected loading would be on the order of 500Ω, so the parallel case was not used in our tests; all measurements were made with series loading. Slight variations in pulse shape were The Microvas source and open circuit voltage were determined by using various combinations of loading resistances and intensity set at 10, with the following results.

| $R_{L1}$/Ω | $R_{L2}$/Ω | $R_s$/Ω | $V_o$/V | $\Delta V_o$ |
|---|---|---|---|---|
| 2016.7 | 5150.0 | 417.7 | 130.3 | 4.3 |
| 1503.7 | 2016.7 | 425.0 | 134.6 | 6.5 |
| 50.8 | 511.7 | 507.6 | 141.1 | 0.7 |
| 0 | 511.7 | 512.9 | 141.8 | 6.7 |
| 0 | 50.8 | 539.3 | 148.5 | |

Assuming a design goal of a source impedance of 500Ω with an open circuit voltage of 140, adjustments were made to achieve this with a load impedance of 500 Ω.

Figure 13:
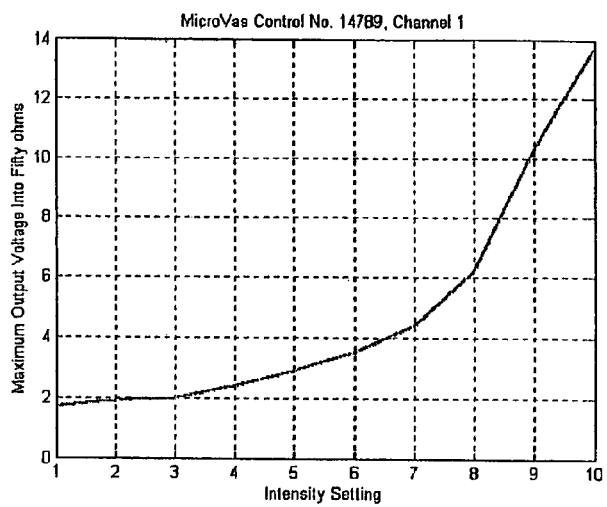
FIG. 13 is a graphic representation of the nonlinear relationship of the machine output voltage to the intensity level.
Figure 14:
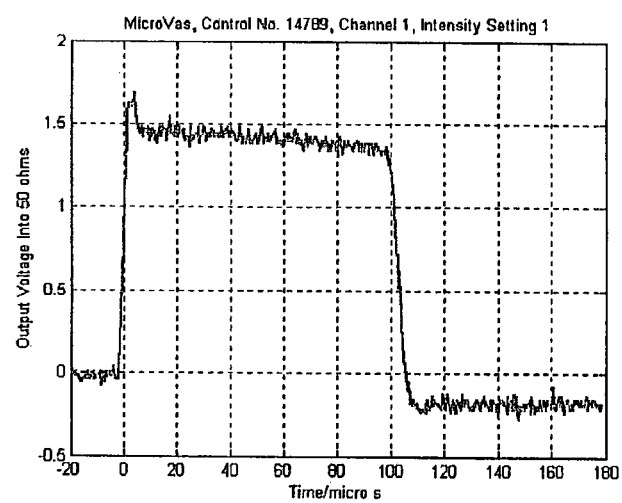
FIG. 14 is an expanded time scale graphic representation of the positive pulse waveform characteristics at low intensity level.
Figure 15:
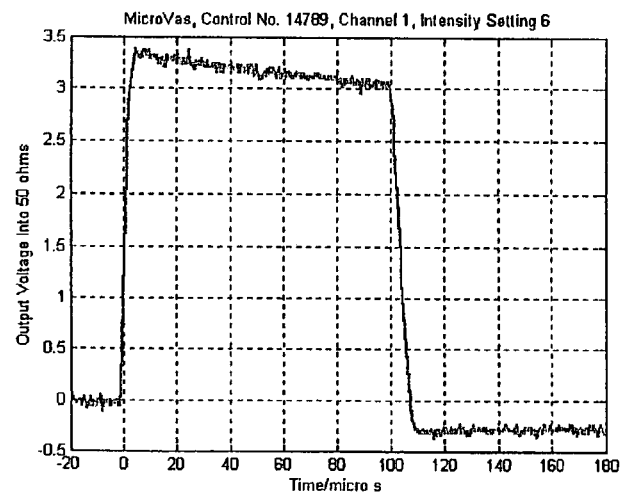
FIG. 15 is an expanded time scale graphic representation of the positive pulse waveform characteristic at a mid-range intensity level.
Figure 16:
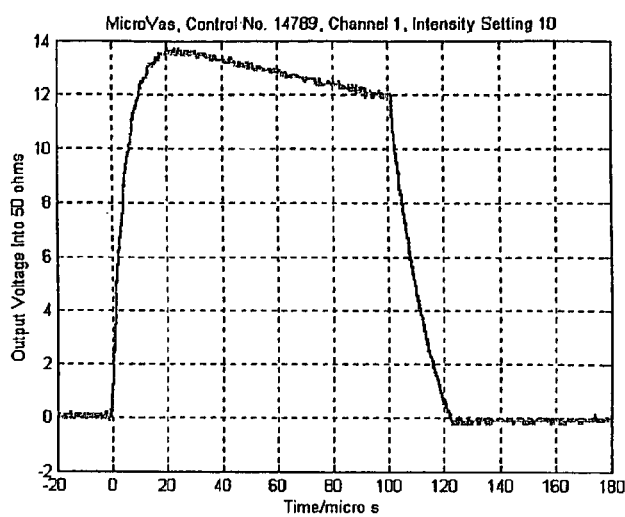
FIG. 16 is an expanded time scale graphic representation of the positive pulse waveform characteristics at a high intensity level.

As shown in FIG. 13, the output voltage is a nonlinear function of the intensity setting. Clearly, the numbers associated with the intensity setting potentiometer are not representative of the relative applied voltages. The variation of waveform characteristic with respect to intensity setting is represented by FIGS. 14 (low intensity), 15 (mid-range intensity) and 16 (full intensity).

While there is some indication that the wave shape has some degree of significance, in which case variation in pulse shape with intensity is an undesirable effect, there is more importantly an indication that spectral content is significant and, as shown, the preferred envelope of the spectrum is dominated by the pulse width, while the high frequency variations are dominated by the biphasic period. Therefore, the spectrum is not substantially altered by the fine details of the pulse shape so long as it has a reasonable semblance to a rectangular pulse. While there is some variation in pulse width, it is not of sufficient magnitude to be significant. This also applies to variations from channel to channel.

Figure 17:
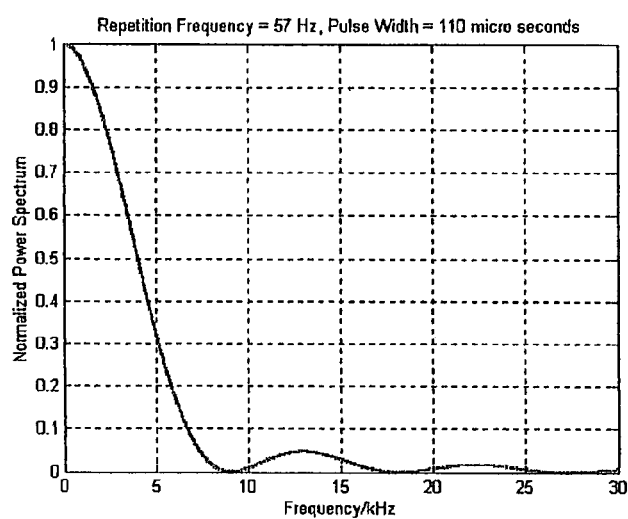
FIG. 17 is a graphic representation of the normalized power spectral density for machine.

While the waveforms observed are not ideally square, they are sufficiently close to provide a reasonably good estimate of their spectral content using the formula presented earlier. For evaluation purposes, the normalized power spectral density, shown in FIG. 17 is of greater interest than the spectral amplitude.

Figure 18:
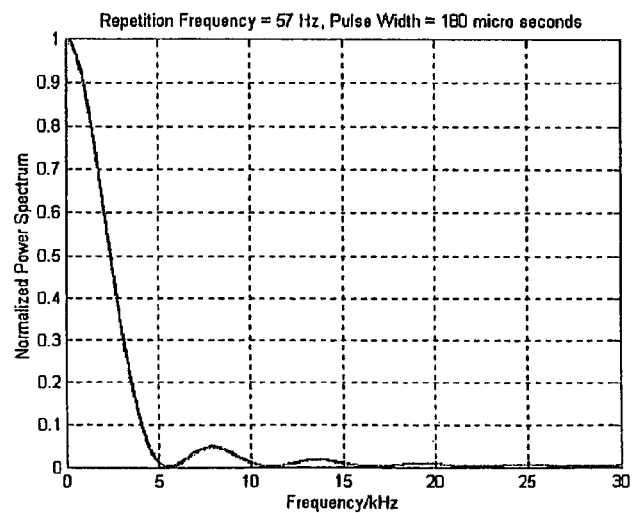
FIG. 18 is a graphic representation of a nominal spectral power density for a preferred embodiment of the machine.
Figure 19:
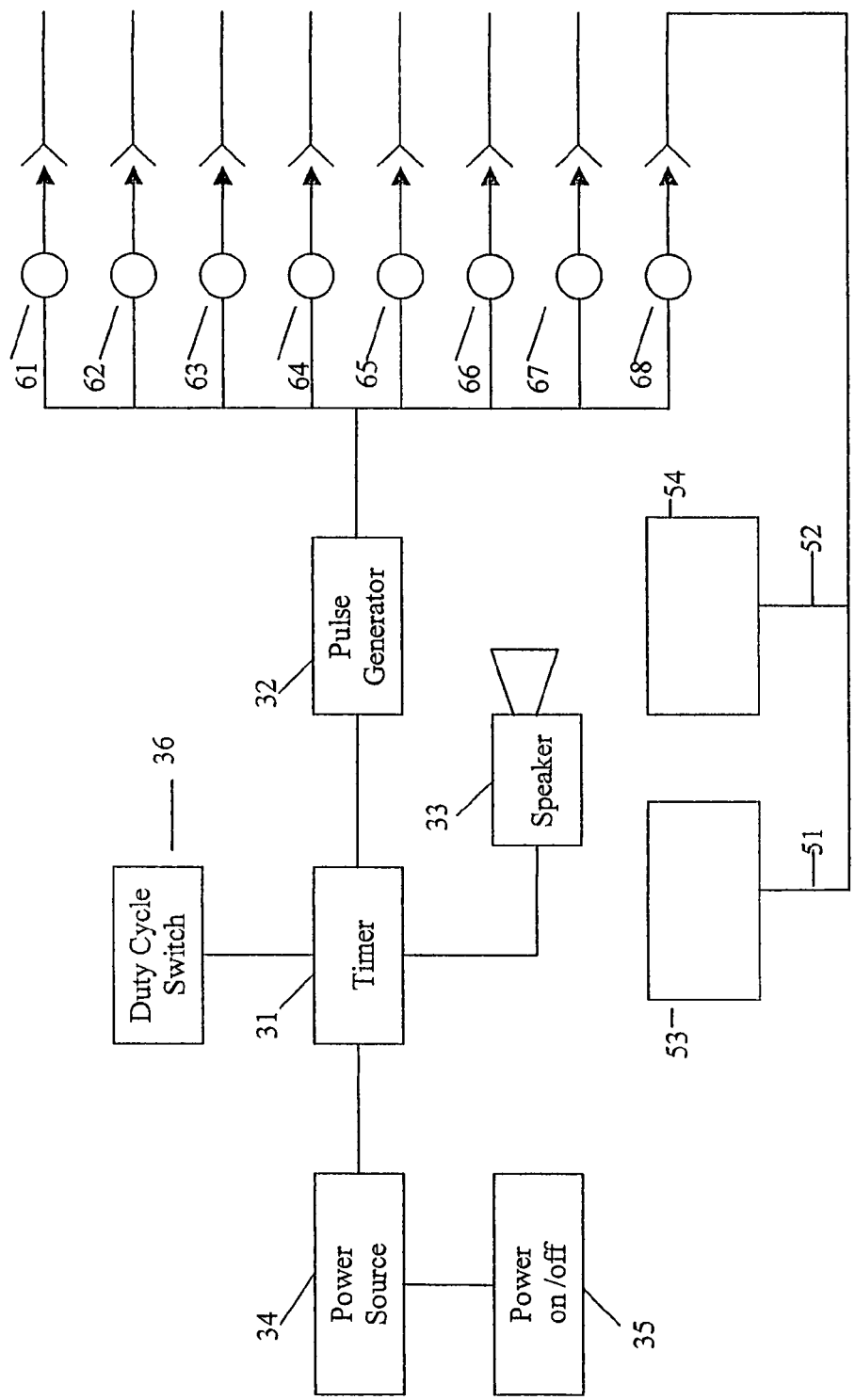
FIG. 19 is a schematic block diagram of the electrical circuit of a preferred embodiment of the machine of FIG. 20.
Figure 20:
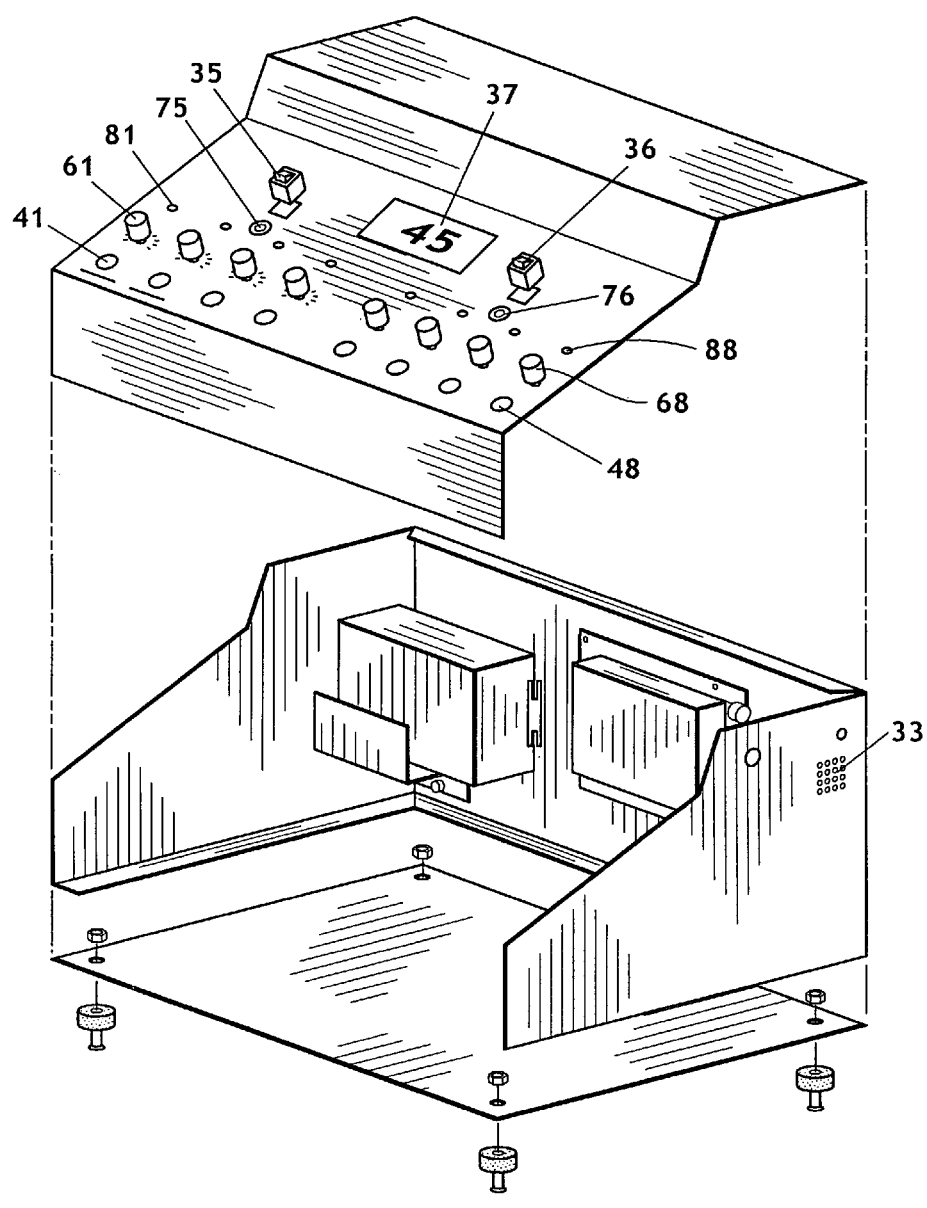
FIG. 20 is a perspective assembly view of a preferred embodiment of the machine of the present invention.
Figure 21:
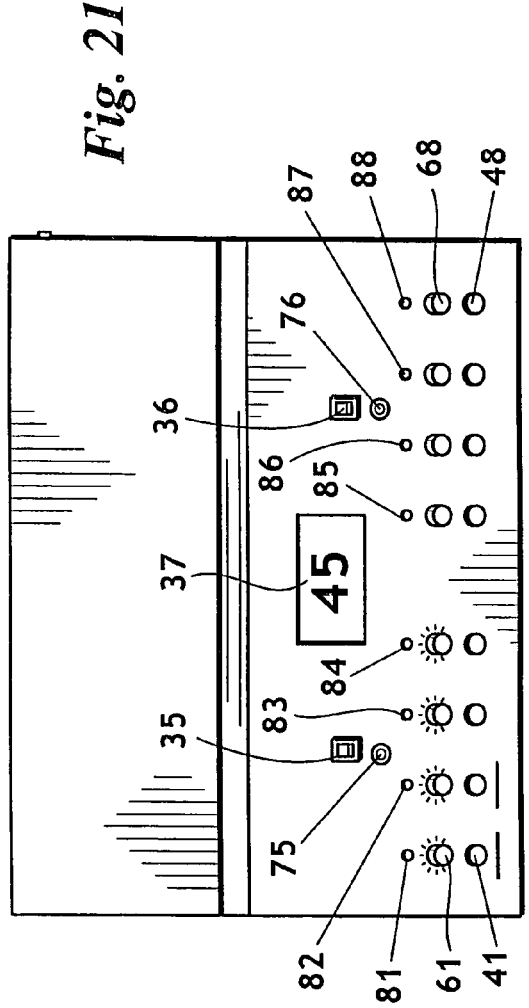
FIG. 21 is a top plan view of the machine of FIG. 20.
Figure 22:
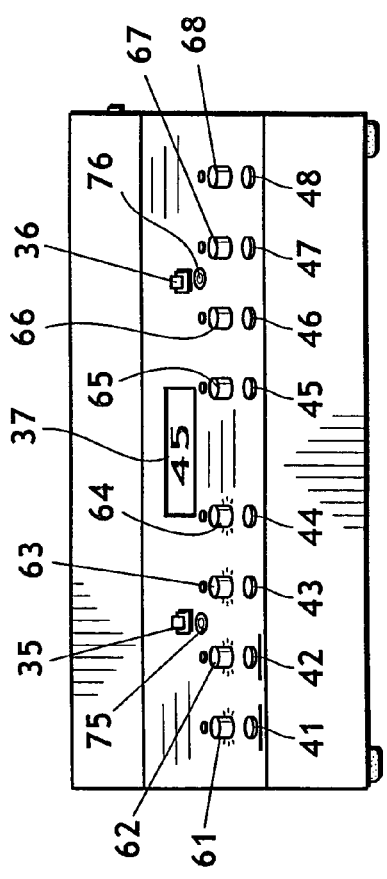
FIG. 22 is a front elevation view of the machine of FIG. 20.
Figure 23:
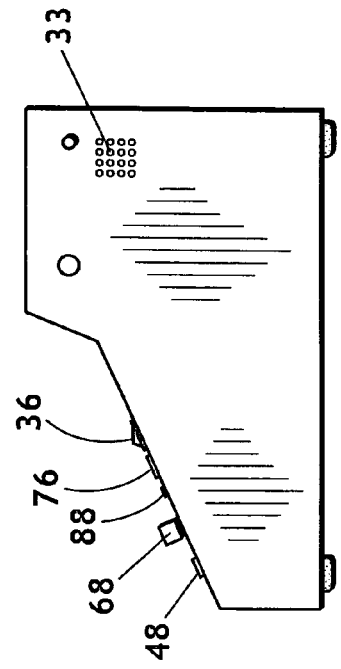
FIG. 23 is a side elevation view of the machine of FIG. 20.

It is possible that radio frequency components could have adverse affects. While the definition of a radio frequency is not precise, radio frequencies are, for this disclosure, deemed to be those above 10 kHz, the upper end of the audio spectrum being about 20 kHz. On this basis, the preponderance of the spectral power is below radio frequencies. The nominal pulse width is 180 μs. The resultant spectrum, shown in FIG. 18, displays no significant radio frequency components.

Based on the above analysis, measurements, and clinical results, the characteristics of an effective biphasic faradic pulse waveform were found to be: duty cycle, 1.5 s on 1.5 s off; repetition frequency, 57 Hz; pulse width, 110 μs.

Figure 24:
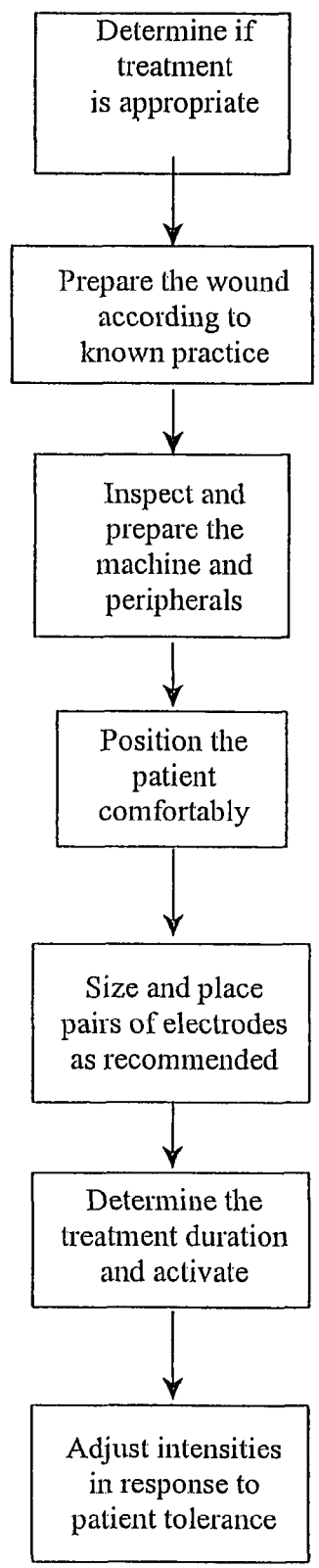
FIG. 24 is a flow chart illustrating the protocol of the present treatment procedure.

Turning to FIGS. 19 through 23, the basic components of the machine include a timer 31 which controls operation of both the pulse generator 33 and a speaker 35. The output of the pulse generator is made available at eight terminals 41 through 48. Each of the terminals 41 through 48 can be connected by a separate pair of leads 51 and 52 to a pair of emitter pads 53 and 54, respectively, as will be hereinafter discussed. The power source 34 for the system is a pair of rechargeable batteries 34, preferably, 12 V/y.5Ah rechargeable sealed-lead-acid batteries. The machine also includes a battery charger connectable to a 120 volt source. The system is configured to interrupt power if the machine is connected to any 120 volt source. Looking at FIGS. 20-22, clinician control of the system involves the power ON/OFF switch 35, a duty cycle ON/OFF switch 36, and eight intensity potentiometers 61 through 68, one for each of the terminals 41 through 48, respectively. The intensity potentiometers 61 through 68 click between an OFF position and an ON position in which the intensity may be varied in ten increments increasing from intensity settings of 1 through 10. The system is configured so that, if any of the intensity potentiometers 61 through 68 are not in the clicked OFF condition, operation of the duty cycle switch 36 will not activate the system. If the power source 34 is sufficiently charged, if the system is not connected to a 120 volt source and if the intensity potentiometers 61 through 68 are all clicked OFF, upon the operation of the power switch 32, power is available to the system under the control of the timer 31. If power is available and the intensity potentiometers are all in the clicked OFF condition, when the clinician initiates the duty cycle by pressing the duty cycle switch 36, the pulse generator 32 begins to deliver the output signal to the output terminals 41 through 48 via the intensity potentiometers 61 through 68. Immediately a digital display 37 on the machine control board indicates the time remaining in the duty cycle in one minute increments. In the preferred embodiment, the duty cycle is set at 45 minutes. When the 45 minute duty cycle has elapsed, the timer 31 will disconnect power to the pulse generator 32 and cause the speaker 33 to give an audible signal indicating that the duty cycle has been completed. The power ON/OFF switch 35 has an associated LED 75 indicating that the system is turned ON. The duty cycle switch 36 has an associated LED 76 which will flash continuously with the pulse status to indicate that the duty cycle is in operation. The system is further configured so that, if the duty cycle is disabled because any one of the intensity potentiometers 61 through 68 is not in the clicked-OFF condition, the duty cycle 76 led will flash rapidly ON and OFF until the condition is corrected. The battery charger power system is preferably a 120V AC @0.25 amps AC power entry module with integral fuse and switch. The power ON/OFF switch 35 and duty cycle switch 36 are rocker type switches The procedure for treatment is described in reference to FIG. 24. First, it must be determined whether the present treatment is appropriate for the particular patient. This protocol is for the treatment of any condition that can benefit from enhanced healing and repair through the mechanisms of increased blood flow, nutrient supply, waste removal and cellular activity. A comprehensive list of treatable conditions is provided at the end of this description, but some major examples include the following:

- a. Diabetic ulcers or ischemic ulcers in the bedfast or neurologically compromised patient are characterized by decreased healing due to ischemia and compromise in the microcirculation, which the present treatment can enhance and remodel;
- b. Large decubiti requiring surgical closure with skin, fat or muscle flaps can benefit from preheating before the closure by improved blood flow, granulation, and epithelialization of wound margins;
- c. Sports injuries including sprains and strains can benefit from more rapid healing due to the enhanced blood flow, the increased activity of the fibroblasts and the reeducation of the entire muscle mass as well as the ligaments and tendons;
- d. Repetitive stress injuries such as carpal tunnel syndrome characterized by an imbalance between the wear and tear in the tissues and an inadequate healing and repair response usually respond rapidly to the present treatment;
- e. Chronic pain syndromes such as fibromyalgia and chronic low back pain benefit from a decrease in pain and an increase in flexibility and function;
- f. Healing time for bone fractures can be decreased due to the increased blood flow as well as the direct stimulation of the bone by the present electrical waveform;
- g. Ischemic rest pain conditions due to arterial insufficiency can be improved with the present treatment;
- h. Degenerative arthritic conditions including osteoarthritis and degenerative joint disease can be improved through the enhanced blood flow and healing of the present treatment;
- i. The present treatment will positively reverse diabetic neuropathy and keep it reversed.
- j. The procedures described herein can be used to increase the effectiveness of chemotherapy treatments, leading to reduction in the chemotherapy deleterious side effects.

To determine the appropriateness of the procedure, inspect the area for ischemic necrosis that is extensive enough to put the patient at risk for infection that would be limb threatening and require surgical intervention. Check for gas gangrene by crepitus to palpation and gas in the limb on x-ray. While the present treatment can improve circulation and the resistance to infection in the limb fairly quickly, if the condition is too advanced with ischemic necrosis and advancing gas gangrene present involving more than a toe or two, it is best to proceed directly to surgical intervention. Manageable cellulitis is not a contraindication. The present treatment can aid in resolving the infection. Any patient with blood clot problems of any kind is a contraindication to the present procedure. The procedure is also inappropriate in cases of deep and superficial thrombophlebitis, pregnancy, and placement of emitter pads above the waist on patients with demand-type pacemakers.

If the present procedure is appropriate proper wound care must be given to the patient with open or infected decubitus following current standards including daily inspection, sterile technique, appropriate debridement, cultures and antibiotics when indicated and proper dressings.

The machine and peripheral equipment should be inspected and prepared for each use. Use one or more clean disinfected pairs of emitter pads soaked in normal sterile saline, but not dripping wet, for each treatment. Following the treatment, rinse the pads in clean water and sterilize them using steam or chemical sterilizing agents. Let the pads air dry out unless they are to be used again immediately. Wipe down the carbon rubber emitter pads and leads with a chemical-sterilizing agent. If the equipment becomes contaminated with blood, pus or bacteria, wipe it down with a damp cloth soaked in a chemical sterilizing agent. For best results charge batteries over night if used during the day.

The patient should be placed in a comfortable position, lying or sitting so the muscles in the area of treatment can remain relaxed. Allow the area of treatment to be exposed, without pressure from the weight of the limb or body, to allow the stimulation of the circulation by the treatment.

Typically, the choice of emitter pads may be round, on the order of one to four inches in diameter, or rectangular on the order of one by two inches to eight by twelve inches, though different configurations and sizes may also be appropriate for specific body contours. Place the largest emitter pads that can be physically placed adjacent to the area to be treated. Use one to four pairs of emitter pads surrounding the area such that each pair cause the current to flow through the area of treatment. Place an additional pair or two pairs of emitter pads on the opposite sides of the large muscle masses of the limb proximal to the area of treatment. This will aid blood flow in the larger vessels that supply the area to be treated and aid in the lymphatic drainage from the area. For example, one emitter pad may be placed over the quadriceps muscle with it's mate placed over the hamstrings about mid body. The emitter pads must be secured with just enough pressure to cause full contact with the skin but not too much such that blood flow might be compromised to the area. Partial emitter pad contact could cause a painful concentration of the current. Ensure that the positive and negative emitter pads do not touch. If this occurs, the current will short between the emitter pads and not provide therapeutic benefit to the patient. Do not place the emitter pads over the heart, neck or head.

It has been experimentally determined that the optimal duration of treatment is 45 minutes twice a day, but a single 45 minute treatment 5 days a week is also effective but taking a longer time to reach full effectiveness. The typical treatment condition would be a severe diabetic ischemic foot ulcer that is in jeopardy of amputation. This will require several weeks of treatment at 45 minutes twice a day. Conditions like carpal tunnel syndrome will require about 10 treatments over a two week period while conditions like acute sprain will respond nicely to 5 or 6 treatments.

All of the electronic parameters have been optimized and the only variable is intensity. When placing the emitter pads 53 and 54 on the patient at the beginning of the treatment, the machine is turned off with all dials 61 through 68 and switches 35 and 36 in the off position. With the power switch 35 on, begin the treatment by arming the timer 31 (hold the duty cycle switch 36 on until the light begins blinking). Set the initial intensity of current to about 3 or 4 on the intensity potentiometer 26, incrementally adjusting upward the current on each set of pads 51 and 52 as the patient tolerates over the first 5 minutes. Do not adjust upward more than one number at a time. The patient will develop a rapid tolerance to the current and there will be a decrease in the impedance of the tissues to the current as the body adjusts to it. About 4-5 initial adjustments will be necessary. Readjust upward to tolerance after the first 10 minutes of the treatment.

Visible muscle contractions need to be achieved when the emitter pads 53 and 54 are applied and positioned correctly. If there is a significant degree of disuse atrophy, active observable muscle contraction may not occur during the initial treatment session. Considerable edema may make it difficult to observe muscle contraction. If there is no perception of contraction either by observation or by palpation of the muscle compartment, after the treatment is underway, then the emitter pad contact point may need to be checked for inadequate conduction of current. Repositioning may be necessary or more saline may need to be applied to the emitter pads 53 and 54 to achieve the desired results. When a patient has extreme neuropathy and claims to feel no electrical current, then the clinician may check the integrity of the emitter pad by turning down the intensity and applying it to the back of his or her own hand. The intensity setting of each channel being utilized should always be increased to the highest setting that the patient comfortably tolerates. At the highest tolerable setting, if there are very robust active muscle contractions, the clinician may opt for decreasing the intensity slightly to avoid fatigue and soreness, particularly in the initial few treatments. Always review the patients perception and impression of the previous treatment as per the treatment chart.

When the 45 minute treatment is over, a buzzer will sound. Then all the intensity switches should be turned off. Remove the equipment and inspect the area for response to the treatment (pink flush is desirable). Check for any complications of infection. Properly dress decubiti following standard wound care protocol. If available, check the transcutaneous pulse oximetry before and after treatment. Document the initial condition of the treated area with diagrams, drawings or pictures as well as at least weekly progress. Take measurements of the diameters of decubiti.

| A Comprehensive List of the various Conditions the Invention Can Successfully Treat |
|---|
| Neuropathy |
| 1. Diabetic neuropathy code insulin dependent or not.
2. Diabetic neuropathy of the Feet
3. Peroneal palsey "drop foot"
4. Bells palsey of the face
5. Trigeminal Neuralgia
6. Sciatica - see condition
7. HIV Neuropathy -
8. Tarsal tunnel syndrome
9. Alcoholic polyneuropathy
10. Hereditary progressive muscle
11. Hereditary progressive muscle dystrophy
12. Paresthesia feet NOS
13. Paresthesia hands NOS
14. Ulnar nerve lesion
15. Foot neuroma metatarsals
16. Chemotherapy induced neuropathy
17. Neuropathy of Pernicious anemia |
| Chronic Pain Syndromes |
| 1. Low back pain
2. Upper back pain due to Fibromyalgia
3. Chronic Tendonitis
4. Shoulders
5. Neck |
| Diabetic Ulcers |
| 1. Toes
2. Heel
3. Calf
4. Tibial surface
5. Plantar surface |
| Venous Insufficiency |
| 1. Stasis Ulcers |
| Pressure Ulcers in Immobile Patients |
| 1. Heel
2. Greater Trochanter
3. Sacrum
4. Ischial Tuberosity |
| Bone Fractures |
| 1. Feet - "marching fracture" or "diabetic fracture" of metatarsals
2. Avulsion fracture distal fibula
3. Femur mid shaft fracture
4. Femur impacted head fracture
5. Radial head fracture
6. Humeral head fracture
7. Humeral mid shaft fracture
8. Navicular fracture in wrist
9. Traumatic compression fracture in lumbar spine
10. Traumatic compression fracture in thoracic spine |
| Osteoporosis/Osteoarthritis/ Degenerative joint disease |
| 1. Spontaneous compression fracture in lumbar spine
2. Spontaneous compression fracture in thoracic spine
3. Chronic hip pain from osteoporosis |

-continued

A Comprehensive List of the various Conditions the Invention Can Successfully Treat 4. Degenerative arthritis knee
5. Degenerative arthritis hip
6. Degenerative arthritis ankles
7. Osteoarthritis hand
8. Generalized bone healing (not a diagnosis)

Ischemic Rest Pain due to Arterial Insufficiency

1. Feet
2. Calf
3. Thigh

Disuse atrophy

1. Bedfast conditions - lower and upper extremity wasting
2. Muscle wasting conditions such as multiple sclerosis
3. Muscle atrophy
4. Parkinsonism dementia Paraplegia and Quadriplegia 1. Ischial tuberosity decubitus from wheelchair Repetitive Stress Syndromes 1. Carpal Tunnel syndrome
2. Lateral epicondylitis (Tennis elbow)
3. Medial epicondylitis (golfers elbow)
4. Plantar Fasciitis
5. Costochondritis Traumatic Peripheral Nerve Injuries 1. Hand
2. Forearm
3. Upper Arm
4. Lower legs Sports Injuries & Acute Sprain/Strain 1. Ankle lateral sprain first or second degree
2. Knee strain medial or lateral collateral ligament
3. Wrist
4. Shoulder strain
5. Elbow
6. Neck acute cervical strain
7. Pulled Hamstring Miscellaneous 1. Brown recluse spider bites
2. Localized second and third degree burns - can't code
3. Post radiation burns ulcerated or poorly healing
4. Stasis ulcers due to venous insufficiency
5. Post polio syndrome
6. Lymphadema
7. Post radiation treatment trauma
8. Malignant tumors in conjunction with chemotherapy Thus, it is apparent that there has been provided, in accordance with the invention, a procedure and machine that fully satisfy the objects, aims and advantages set forth above. While the invention has been described in conjunction with a specific embodiment thereof, it is evident that many alternatives, modifications and variations will be apparent to those skilled in the art and in light of the foregoing description. Accordingly, it is intended to embrace all such alternatives, modifications and variations as fall within the spirit of the appended claims.

What is claimed is:

1. A procedure for treatment of human and animal tissues surrounding articular joints evidencing symptoms of fibromyalgia comprising the steps of:
   identifying an articular joint evidencing symptoms of fibromyalgia;
   sandwiching the tissue surrounding the identified articular joint between one or more pairs of opposed emitter pads in contact with the skin; and
   applying a biphasic pulse sequence to the pairs of emitter pads to stimulate deep layered muscle contractions in the sandwiched tissue.

2. A procedure according to claim 1, said biphasic pulse being rectangular and having a waveform with nominal parameters including a duty cycle of approximately 1.5 seconds on and 1.5 seconds off.

3. A procedure according to claim 2, said nominal parameters further including a repetition frequency of approximately 57 Hz.

4. A procedure according to claim 2, said nominal parameters further including a pulse width of approximately 110 microseconds.

5. A procedure according to claim 1 further comprising the steps of:
   setting the intensity of the biphasic pulse sequence at an initial level; and
   incrementally increasing the intensity in response to the tolerance level of the patient.

6. A procedure according to claim 2, said nominal parameters further including a pulse period of approximately 18 milliseconds.

7. A procedure according to claim 6, said nominal parameters further including a time between initiation of positive and negative pulses of approximately 9 milliseconds.

8. A procedure according to claim 2, said nominal parameters including a peak open circuit voltage of approximately 140 volts with an output impedance of approximately 500 ohms.

9. A procedure for treatment of human and animal tissue surrounding articular joints evidencing symptoms of fibromyalgia comprising the steps of:
   identifying an articular joint evidencing symptoms of fibromyalgia;
   sandwiching the tissue surrounding the identified articular joint between one or more pairs of opposed emitter pads in contact with the skin; and
   applying a pulse sequence to the pairs of emitter pads to stimulate deep layered muscle contractions in the identified tissues, said pulse sequence being a biphasic rectangular pulse sequence having a waveform with nominal parameters including a duty cycle of approximately a 1.5 seconds on and 1.5 seconds off, a repetition frequency of approximately 57 Hz, and a pulse width of approximately 110 microseconds.

10. A procedure according to claim 9, said nominal parameters further including a time between initiation of positive and negative pulses of 9 milliseconds.

11. A procedure according to claim 10, said nominal parameters including a peak open circuit voltage of approximately 140 volts with an output impedance of approximately 500 ohms.

* * * * *